United States Patent [19]

Capetanopoulos

[11] Patent Number: 5,741,413
[45] Date of Patent: Apr. 21, 1998

[54] GAS SENSORS AND METHOD OF USING SAME

[75] Inventor: Constantine Dean Capetanopoulos, Dobbs Ferry, N.Y.

[73] Assignee: Sem Corporation, Westbury, N.Y.

[21] Appl. No.: 670,425

[22] Filed: Jun. 26, 1996

Related U.S. Application Data

[63] Continuation-in-part of Ser. No. 358,915, Dec. 19, 1994, abandoned.

[30] Foreign Application Priority Data

Dec. 18, 1993 [GB] United Kingdom .................. 9325916

[51] Int. Cl.[6] .................................. G01N 27/404
[52] U.S. Cl. .................... 205/783; 204/415; 205/775; 205/781; 205/782.5; 205/786.5
[58] Field of Search .............. 204/415; 205/782, 205/782.5, 783

[56] References Cited

U.S. PATENT DOCUMENTS

| | | |
|---|---|---|
| 3,429,784 | 2/1969 | Molloy .................. 204/415 |
| 4,505,784 | 3/1985 | Mund et al. ............ 204/415 |
| 4,829,809 | 5/1989 | Tantram et al. . |
| 4,833,909 | 5/1989 | Matthiessen . |
| 4,897,162 | 1/1990 | Lewandowski et al. .......... 204/153.17 |
| 5,092,980 | 3/1992 | Maurer et al. . |

OTHER PUBLICATIONS

TM Technisches Messen, vol. 58, No. 2, pp. 71–74, Feb. 1991.

European Search Report, Apr. 10, 1995.

*Primary Examiner*—T. Tung
*Attorney, Agent, or Firm*—Watson Cole Stevens Davis, P.L.L.C.

[57] ABSTRACT

A method of calibrating and using a device for the determination of the concentration of an active gas in a mixture of gases wherein the device incorporates a gas sensor (4) and has gas diffusion barrier means (A) and (B), one of which may be closed by a valve (12). The signal from the sensor is recorded at first and second times after closing the valve, and a value for the concentration of an active gas is calculated from the signals and the time difference.

16 Claims, 2 Drawing Sheets

5,741,413

GAS SENSORS AND METHOD OF USING SAME

This Application is a continuation-in-part of my U.S. patent application Ser. No. 08/358,915, filed Dec. 19, 1994 and now abandoned.

BACKGROUND OF THE INVENTION

This invention concerns improvements in gas sensors, and in particular has reference to a method of calibrating such sensors and a method for determining the level of an active gas in a gas mixture.

U.S. Pat. No. 4,829,809 describes an electrochemical gas sensor device incorporating a sealable chamber of known volume for a gas comprising an unknown quantity of an active gas. By sealing the chamber and then measuring the sensor output at two times, it is possible to calculate the concentration of the active gas, and to calculate therefrom the sensitivity of the sensor. This technique can operate with a variety of sensors specific for different active gases, characteristic of which is carbon monoxide. The teaching of U.S. Pat. No. 4,829,809 is incorporated herein by reference.

The use of electrochemical sensors for determining levels of CO in flue gases from boilers is now well established in control systems for assessing the boiler efficiency and hence improving overall combustion efficiency. There are periods of boiler operation, however, such as during start-up when boiler tuning is significantly deviate from optimum, or when a regulation requires periodic measurements upstream of a flue gas conditioning unit in order to check its operational efficiency, in which the concentration of CO is very much higher than normal. Under such conditions, the electrochemical sensor can be swamped or saturated with active gas and will produce signals that are non-linear, leading to inaccurate readings.

U.S. Pat. No. 5,092,980 describes a modified electrochemical cell having a diffusion barrier of variable area, to give the sensor an increased operational range. This operates by altering the sensitivity of the sensor in order to give different output signal slopes with gas concentration, operating valves to change the area of a diffusion barrier in the event of an overload of the sensor, detected by a comparator comparing sensor output with a predetermined limit value.

SUMMARY OF THE INVENTION

The present invention aims to provide an electrochemical sensor device capable of determining levels of active gas in a gas mixture by the use of valve means but operating in a fundamentally different way to the device disclosed in U.S. Pat. No. 5,092,980.

It will be realised that a gas sensor which produces a signal proportional to the rate of reaction of an active gas, reflects a situation in which active gas is being consumed by the reaction. The invention disclosed in U.S. Pat. No. 4,829,809 uses a chamber of volume of 1 to 200 cm$^3$, eg about 12 cm$^3$, and teaches that this volume must be closed off to the gas mixture before measurements are taken. Indeed the method adopted by Tantram involves the use of a chamber of known volume which is purged with a test gas. The chamber is attached to a galvanic sensor which provides an electrical current output proportional to the concentration of active gas in the chamber, the chamber being located upstream side of the sensor's controlling diffusion barrier. During the coulometric calibration measurement according to Tantram et al the gas purge is stopped and the chamber is sealed, thus entrapping a known amount of gas in communication with the sensor. Due to the electrical reaction at the sensor electrode, gas is consumed from the chamber and the sensor's output current decays. Using the time constants of this decay, the chamber volume and other parameters, Tantram et al were able to derive both the gas concentration and sensor sensitivity values.

Tantram teaches that the chamber is completely sealed and the mathematical relationship he derived assumed the chamber to be perfectly sealed in the calibration mode when there is no gas purge of the chamber, in which case the sensor current would approach asymptotically to a virtually zero reading, given sufficient time. Any background current from the sensor or leakage of gas into the sealed chamber would represent an error.

It has unexpectedly been found that similar calculations to those disclosed in said USP can give values for concentration which are of practical use, simply by closing or partially closing access of gas into the sensor through a diffusion barrier. We have thus realised that the sensor sensing element 'sees' a constant concentration of active gas internally, and if the supply of gas is restricted or terminated, the sensing element will continue to consume the tiny quantity of gas held within the sensor, and produce a declining output signal. It is also significant that the present invention operates successfully in some embodiments which still have an open, albeit restricted, gas diffusion barrier.

An object of the present invention is to provide a simpler means of calibrating a gas sensor without the need to use a fixed known volume of gas.

A further object of the present invention is to provide a device incorporating a gas sensor which facilitates the calibration of the gas sensor and which affords ease of practical use coupled with the ability to self-test for continuing accuracy during use.

In a first aspect of the invention there is provided a method of calibrating a device for determining the concentration of an active gas in a gas mixture the device comprising a gas sensor which consumes active gas by reaction at a sensing element and which produces an output signal proportional to the rate of reaction of active gas, the sensor having a gas diffusion barrier means between the gas mixture and the sensing element, valve means actuable to close or restrict said gas diffusion means, means for recording output signals from the sensor and means for processing said first and second output signals, wherein the method of calibrating the gas sensor includes the steps of passing a gas of known concentration at constant temperature and pressure over the sensor to provide a constant output from the sensor, actuating the valve means to close or restrict the gas diffusion barrier means, recording a first output signal at a first time subsequent to the closing or restricting of said gas diffusion barrier means, recording a second output signal at a second time subsequent to the first time, recording the time interval therebetween, and processing the output signals and the time interval to calculate a constant for the device at constant temperature and pressure for the active gas.

According to a second aspect of the invention there is provided a method for determining the concentration of an active gas in a gas mixture using a device comprising a gas sensor which consumes active gas by reaction at a sensing element and which produces an output signal proportional to the rate of reaction of active gas, the sensor having a gas diffusion barrier means between the gas mixture and the sensing element, valve means actuable to close or restrict said gas diffusion means, means for recording output signals from the sensor and means for processing said first and second output signals, wherein the method including the steps of passing the active gas over the gas sensor, actuating the valve means to close or restrict the gas diffusion barrier means, recording a first output signal at a first time subsequent to the closing or restricting of said gas diffusion barrier means, recording a second output signal at a second time subsequent to the first time, recording the time interval therebetween, and processing the output signals and the time interval utilising the constant calculated according to the first aspect of the invention thereby to calculate a value for the concentration of active gas.

Conveniently, the gas is passed over a sensor such as a galvanic electrochemical gas sensor having a sensing element capable of producing an output signal proportional to the rate of reaction of said active gas at the sensing element, the sensor having gas diffusion barrier means for example first and second gas diffusion barriers, the first barrier having a lower resistance to flow of gas to the sensing element than the second barrier. The gas diffusion barrier means is closed or restricted to prevent or restrict gas flow therethrough, a first output signal is generated from the sensor and recorded at a time subsequent to the closure or restriction of the barrier means, and a second output signal is generated from the sensor and recorded at a time subsequent to the recordal of the first output signal. The output signals and the time interval between the first and second output signals are processed to calculate a value for the concentration of active gas using the constant previously established.

The galvanic electrochemical cell is a particularly useful type of gas sensor and the majority of the description hereinafter shall refer to such cells.

However, there exist other gas sensors which may be used, such as a pellistor which measures the concentration of a flammable gas by exothermic reaction of the flammable gas with oxygen on a catalytic bead.

It has been found that one of the several equations described in U.S. Pat. No. 4,829,809 is particularly useful to permit the calculation required in the use of the present invention. In particular, and starting from a gas of known concentration, the equation:

$$C_0 = \frac{S_t}{S_{2t}} \times S_t \times \frac{t}{A} \times \ln \frac{S_t}{S_{2t}}$$

in which $C_0$ is the concentration of active gas (usually in ppm) $S_t$ is the cell output signal at a first time, in uA, $S_{2t}$ is the cell output signal at a second time, in uA t is the time difference between the first and second times, in seconds, and A is a constant of the device at constant temperature and pressure, for a given gas (the units for A will depend upon the units chosen for the other measurands) enables a value for A to be determined. In turn, a predetermined value for A for a particular device may be used with the above equation to allow the calculation of a concentration with the simplest of measurements of two sensor output signals and a time difference. Two measurements have been found to give sufficient accuracy for most practical purposes. If greater accuracy is required, however, it is possible to record many more than two sensor output signals and times, and to improve the accuracy of the calculation by statistical techniques.

The calculation may be done manually, using a calculator, or preferably using a dedicated microprocessor, or the microprocessor which is part of a controller/processor as may be found in a boiler efficiency monitor and controller.

A particularly preferred embodiment of device for determining the concentration of an active gas in a gas mixture in accordance with the present invention, comprises a gas sensor having a sensing element and capable of producing an output signal proportional to the rate of reaction of the active gas at the sensing element, which sensor incorporates at least first gas diffusion barrier means and optionally second gas diffusion barrier means (in which case said first gas diffusion barrier means has a lower resistance to flow of gas to the sensing electrode than said second gas diffusion barrier means), valve means for closing or restricting said first gas diffusion barrier means, means for recording a first output signal from the sensor at a first time subsequent to the closing of the valve means, and for recording a second output at a second time subsequent to said first time, and means for processing the said first and second output signals with the time interval between said first and second times to calculate a value for active gas concentration.

The gas diffusion barrier means are suitably capillaries, or orifices, of different diameters, although the sensor designer may choose other types of gas diffusion barriers such as described in Chapter 6 of "Techniques and Mechanisms in Gas Sensing", Ed P T Moseley et al, including multiporous barriers and solid membranes (this chapter is a particularly useful chapter describing electrochemical sensor cells). There may, for example, be a first gas diffusion barrier means comprising a plurality of capillaries or orifices, with a second gas diffusion barrier means comprising a single gas entry in the form of a capillary or orifice. Other possible arrangements include using a single capillary as the first gas diffusion barrier and multiple capillaries as the second gas diffusion barrier, or using multiple capillaries (not necessarily the same number) for both first and second gas diffusion barriers. Especially in the case of a single capillary, it is relatively straightforward to incorporate a valve seat in the mouth of the capillary. Alternatively, a valve member may contact and seal the mouth of the capillary. In the case of multiporous barriers or other extended surface diffusion barriers, a valve means may cover and seal part only of the barrier, which is equivalent to closing first barrier means and leaving second barrier means free for passage of gas.

The sensor cell itself is of a type known in the art.

The valve is conveniently a plunger or piston mating with the valve seat, and actuated by a piston for arrangement operated by a solenoid, although any other means which gives consistent and reliable operation such as pneumatic pressure or micro-motor may be used. Valve means other than a piston or plunger that may be used include disc valves or sliding valves.

The actuation of the valve means may be manual, for example by a button or lever, or may be initiated by a control means at pre-determined times (to check sensitivity, for example).

The invention may find utility in safety applications, where in general there is little or no active gas present, and a sensor is present to initiate an alarm or other signal upon the appearance of the active gas at higher than permitted or desired levels, or in emission control. It has particular utility in the measurement of CO in flue gases, it is by no means limited thereto, and may be used for the accurate determination of active gases such as may be contained in a gas cylinder, or generated chemically or by electrochemical means. Gas cylinders frequently contain a mixture of an active gas with an inert gas, and experience has shown that the nominal gas composition may be inaccurate by up to about 10% because of reaction of the active gas and/or the difficulties of blending accurately, and inaccuracies are more often seen at low volumetric concentrations.

BRIEF DESCRIPTION OF THE DRAWINGS

The method and device of the present invention will now be described with reference to the accompanying drawings in which.

DESCRIPTION OF PREFERRED EMBODIMENT

Figure 1:
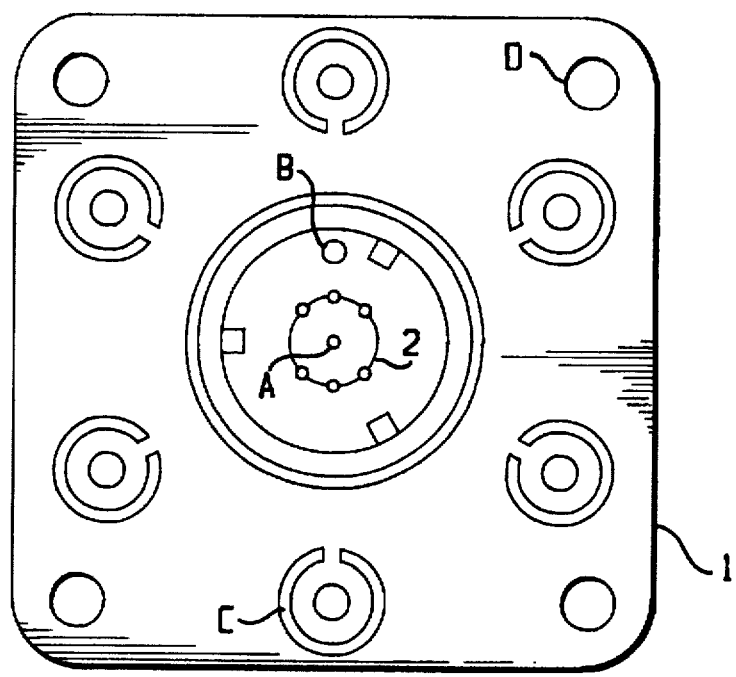
FIG. 1 is a top view of a gas sensor component.

Referring to the gas sensor component in FIG. 1, this is in the form of a plastics top plate 1 which acts as a top plate of an electrochemical gas sensor, for example as manufactured by City Technology Limited of Portsmouth, England. (The normal top plate of a gas sensor incorporates a gas diffusion barrier in the form of a capillary (or may contain several capillaries depending upon the particular sensor), and is mounted directly in contact with a diffusion membrane which separates gas from liquid electrolyte.) In accordance with the invention, plate 1 has a central area 2, incorporating a set of capillaries A, having a central capillary and six surrounding capillaries, together forming the first gas diffusion barrier. Offset in the central area is a further capillary B forming the second gas diffusion barrier. In the particular embodiment shown, each capillary A has a diameter of 0.9 mm, and the capillary B has a diameter of 1.35 mm. In plate 1, holes C are used to secure the plate together with the other components of the electrochemical cell, and holes D are used to mount the cell in a desired position. The plate 1 as shown has been tested with an NO sensor.

Figure 2:
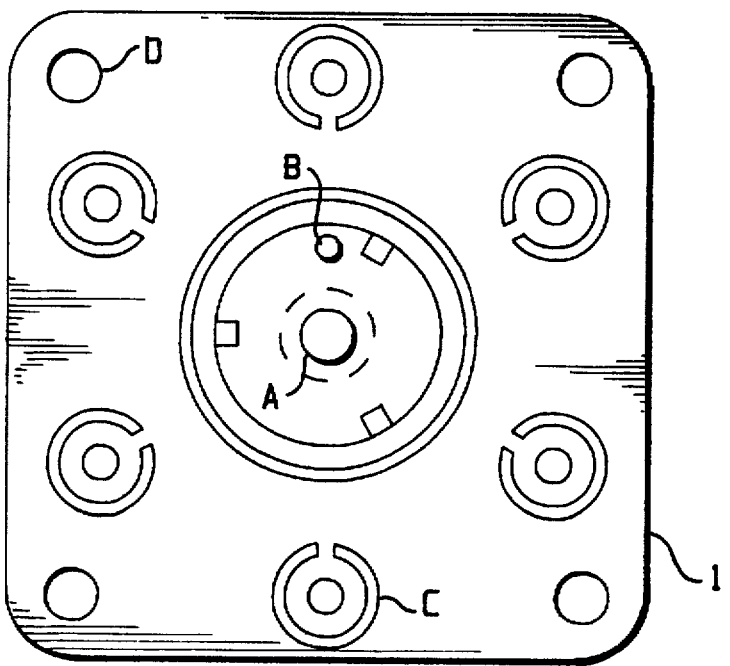
FIG. 2 is a top view of an alternative gas sensor component.

The alternative component shown in FIG. 2 is of the same general description as that of FIG. 1, and identical reference numerals are used for identical parts. In this instance, a single central capillary A is used, and the diameters, in mm, of both capillaries A and B are given below for different gases (for which different gas sensors, themselves having different characteristics, must be used):

| GAS | CAPILLARY A | CAPILLARY B |
| --- | --- | --- |
| $SO_2$ | 3.9 | 1.2 |
| $NO_2$ | 5.3 | 2.0 |
| CO | 0.81 | 0.326 |

Figure 3:
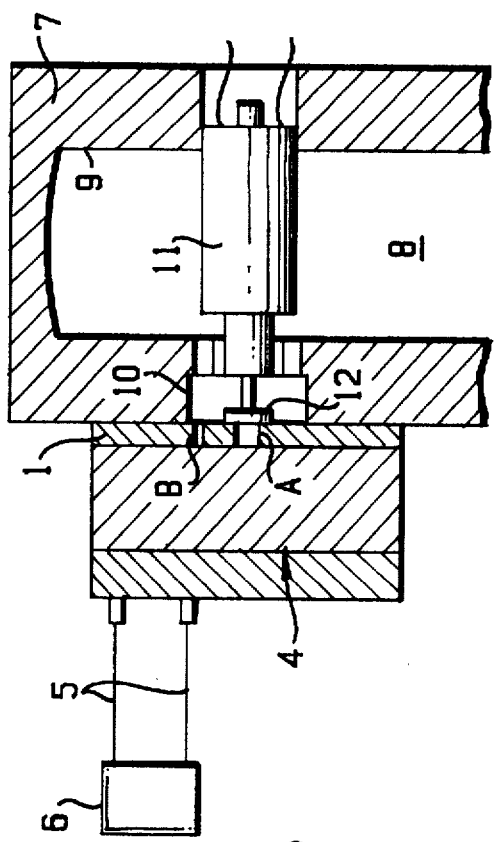
FIG. 3 is a sectional side view of a gas sensor device according to the invention.

Referring now to FIG. 3, the plate 1 is mounted onto a gas sensor 4, shown schematically, having output leads 5 connected to a signal processor 6 suitably a commercial mircoprocessor. The signal microprocessor may communicate with a display unit (not shown) or retain signal values and calculated concentrations for later access by a user.

The sensor cell and plate 1 are mounted in a gas flow housing 7 for conveying gas samples to the sensor. The housing has a main gas flow channel 8 and a gas exit 9, and a gas sampling space 10 communicates with the main channel 8. Also mounted in the housing 7 is a solenoid device 11 having a plunger carrying a valve member 12 made of stainless steel, although other materials which are inert under the conditions of use may be used, and these may be Ni-plated steel, PTFE or the like. The solenoid is shown in a position in which the valve member contacts the central area of plate 1 and closes off the first diffusion barrier.

Figure 4:
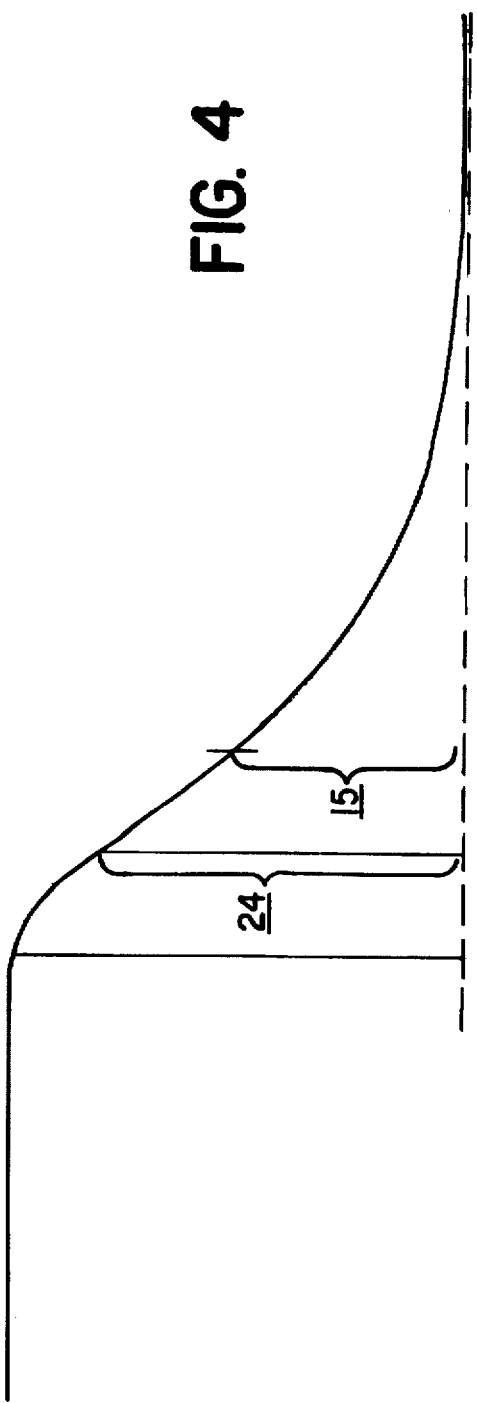
FIG. 4 is a trace of a sensor output signal.

In accordance with the method of the invention the gas sensor was calibrated to calculate a constant for the device. Thus a reference mixture of gas containing an active gas, in this instance CO, and air was employed, the concentration of CO being 187 ppm. The gas was caused to flow through the device with access to the sensor 4 from which a constant output signal was achieved. The solenoid device 11 was actuated and the valve member 12 sealed of the first gas diffusion barrier A, at which time the sensor signal began to decay towards another constant value, as shown in FIG. 4. Signals and time differences were processed using the equation given above to give a value for constant A of 1.463.

The device was then used in accordance with the methods of the invention in the same manner to check its accuracy with another gas whose nominal concentration of CO in $N_2$ was 2000 ppm. It was observed that the output signal from the sensor cell decayed in the same way, and that the slope of the curve was identical. Utilising the value of A previously calculated in the said equation, a concentration of 1969 ppm was calculated.

In general, the device of the invention is calibrated in accordance with the method of the invention upon installation using a standard gas of known concentration. It may be arranged to self check its sensitivity during operation using standard gases, or even a flue gas of unknown constituency providing that actuation of the valve means is not effected until the sensor output signal has been constant for a significant time such as several minutes. Furthermore the inventor has found that it is not necessary to seal all the sensor's capillaries during a calibration check, but instead it is possible to analyse the sensor signal relaxation from a high sensitivity, ie with the piston open, to a low sensitivity, ie with the piston closed.

A particular, although not exclusive, use envisaged is in association with combustion monitoring, especially where a flue gas conditioning unit is fitted, which acts to reduce regulated emissions. A CO or other monitor may be fitted downstream of the conditioning unit, and comprises a device according to the invention precalibrated in accordance with the principal method of the invention. Such a monitor may be periodically moved to upstream of the conditioning unit, or even to check the operation of the monitor. The device can then be used with partial blocking of the gas diffusion barrier as a dual range monitor.

The present invention affords a simple method of calibrating a device for determining the concentration of an active gas by effectively using the internal volume of the sensor downstream of the diffusion barrier, in sharp contrast to Tantram who utilises a fixed and known volume chamber upstream of the diffusion barrier. In this respect, the device is accordingly simpler, more compact and more convenient to use than the teachings of Tantram.

I claim:

1. A method of calibrating a device for determining the concentration of an active gas in a gas mixture the device comprising a gas sensor which consumes active gas by reaction at a sensing element and which produces an output signal proportional to the rate of reaction of active gas, the sensor having a gas diffusion barrier means between the gas mixture and the sensing element, valve means actuable to close or restrict said gas diffusion means, means for recording output signals from the sensor and means for processing said output signals, wherein the method of calibrating the gas sensor includes the steps of passing a gas of known concentration at constant temperature and pressure over the sensor to provide a constant output from the sensor, actuating the valve means to close or restrict the gas diffusion barrier means, recording a first output signal at a first time subsequent to the closing or restricting of said gas diffusion barrier means, recording a second output signal at a second time subsequent to the first time, recording the time interval therebetween, and processing the output signals and the time interval to calculate a constant for the device at constant temperature and pressure for the active gas.

2. A method for determining the concentration of an active gas in a gas mixture using a device comprising a gas sensor which consumes active gas by reaction at a sensing element and which produces an output signal proportional to the rate of reaction of active gas, the sensor having a gas diffusion barrier means between the gas mixture and the sensing element, valve means actuable to close or restrict said gas diffusion means, means for recording output signals from the sensor and means for processing said output signals, wherein the method includes the steps of passing the active gas over the gas sensor, actuating the valve means to close or restrict the gas diffusion barrier means, recording a first output signal at a first time subsequent to the closing or restricting of said gas diffusion barrier means, recording a second output signal at a second time subsequent to the first time, recording the time interval therebetween, and processing the output signals and the time interval utilizing a constant for the device calculated according to the method of claim 1 thereby to calculate a value for the concentration of active gas.

3. A method for determining the concentration of an active gas in a gas mixture using a device comprising a galvanic electrochemical gas sensor which consumes active gas by reaction at a sensing element and which produces an output signal proportional to the rate of reaction of active gas, the sensor having a gas diffusion barrier means between the gas mixture and the sensing element, valve means actuable to close or restrict said gas diffusion means, means for recording output signals from the sensor and means for processing said output signals, wherein the method including the steps of passing the active gas over the gas sensor, actuating the valve means to close or restrict the gas diffusion barrier means, recording a first output signal at a first time subsequent to the closing or restricting of said gas diffusion barrier means, recording a second output signal at a second time subsequent to the first time, recording the time interval therebetween, and processing the output signals and the time interval utilizing a constant for the device calculated according to the method of claim 1 thereby to calculate a value for the concentration of active gas.

4. A method according to claim 1 in which the constant is calculated using the equation:

$$C_0 = \frac{S_t}{S_t} \times S_t \times \frac{t}{A} \times \ln \frac{S_t}{S_{2t}}$$

in which $C_0$ is the concentration of active gas in parts per million $S_t$ is the sensor output signal at the first time, in uA, $S_{2t}$ is the sensor output signal at a second time, in uA t is the time difference between the first and second times, in second, and A is a constant of the device at constant temperature and pressure, for a given gas.

5. A method for determining the concentration of an active gas in a gas mixture using a device comprising a gas sensor which consumes active gas by reaction at a sensing element and which produces an output signal proportional to the rate of reaction of active gas, the sensor having a gas diffusion barrier means between the gas mixture and the sensing element valve means actuable to close or restrict said gas diffusion means, means for recording output signals from the sensor and means for processing said output signals, wherein the method includes the steps of calibrating the device according to the method of claim 1, passing the active gas over the gas sensor, actuating the valve means to close or restrict the gas diffusion barrier means, recording a first output signal at a first time subsequent to the closing or restricting of said gas diffusion barrier means, recording a second output signal at a second time subsequent to the first time, recording the time interval therebetween, and processing the output signals and the time interval utilizing a constant for the device calculated according to the method of claim 1 thereby to calculate a value for the concentration of active gas.

6. A method according to claim 5, wherein the gas sensor is a galvanic electrochemical sensor.

7. The device of claim 5, wherein the gas diffusion barrier means comprises a plurality of capillaries, the valve means comprises a plunger actuated by a piston rod arrangement operated by a solenoid to seal all or less than all of the capillaries while calibrating the device.

8. The method of claim 1, wherein the gas diffusion barrier means comprises a plurality of capillaries, the valve means comprises a plunger actuated by a piston rod arrangement operated by a solenoid to seal all or less than all of the capillaries while calibrating the device.

9. A device for determining the concentration of an active gas in a gas mixture comprising a gas sensor having a sensing element and capable of producing an output signal proportional to the rate of reaction of the active gas at the sensing element, which sensor incorporates at least first gas diffusion barrier means, valve means for closing or restricting said at least first gas diffusion barrier means, means for recording a first output signal from the sensor at a first time subsequent to the closing of the valve means, and for recording a second output at a second time subsequent to said first time, and means for processing the said first and second output signals with the time interval between said first and second times to calculate a value for active gas concentration.

10. A device according to claim 9 in which a second gas diffusion barrier means is provided having a higher resistance to flow of gas than said first gas diffusion barrier means.

11. A device according to claim 9 in which the gas sensor is a galvanic electrochemical sensor.

12. A device according to claim 9 in which the gas diffusion barrier means comprises at least one capillary.

13. A device according to claim 12 in which the gas diffusion barrier means is a single capillary.

14. A device according to claim 12 in which the gas diffusion barrier means comprises a plurality of capillaries.

15. A device according to claim 9 in which the valve means comprises a plunger actuated by a piston rod arrangement operated by a solenoid.

16. A device according to claim 9 in which the gas sensor is an electrochemical CO sensor.

* * * * *